(12) United States Patent
Huh

(10) Patent No.: US 7,594,278 B2
(45) Date of Patent: Sep. 29, 2009

(54) MULTI-FUNCTION FACE PROTECTOR

(75) Inventor: Moon Young Huh, Seoul (KR)

(73) Assignee: OTOS Tech Co., Ltd. (KR)

( * ) Notice: Subject to any disclaimer, the term of this patent is extended or adjusted under 35 U.S.C. 154(b) by 164 days.

(21) Appl. No.: 11/535,252

(22) Filed: Sep. 26, 2006

(65) Prior Publication Data
US 2007/0220649 A1 Sep. 27, 2007

(30) Foreign Application Priority Data
Mar. 24, 2006 (KR) .................. 10-2006-0026718

(51) Int. Cl.
A41D 13/00 (2006.01)
(52) U.S. Cl. .............................................................. 2/9
(58) Field of Classification Search .............. 2/206, 2/8, 9, 10, 424, 453, 437, 436, 6.5, 5, 173, 2/169, 15, 422; 128/207.12, 201.24, 206.19, 128/206.15
See application file for complete search history.

(56) References Cited
U.S. PATENT DOCUMENTS

| | | | |
|---|---|---|---|
| 2,881,443 A * | 4/1959 | Barker, Jr. ..................... | 2/9 |
| 4,625,341 A * | 12/1986 | Broersma ..................... | 2/424 |
| 4,856,109 A * | 8/1989 | Desy et al. ..................... | 2/9 |
| 6,996,846 B1 * | 2/2006 | Karapetyan ..................... | 2/9 |
| 2005/0108801 A1 * | 5/2005 | Morgan et al. ..................... | 2/9 |

FOREIGN PATENT DOCUMENTS

EP 1607013 A1 * 12/2005

* cited by examiner

Primary Examiner—Shaun R Hurley
Assistant Examiner—Andrew W Sutton
(74) Attorney, Agent, or Firm—Cantor Colburn LLP

(57) ABSTRACT

Disclosed herein is a face protector having a protective shade that enables the worker to perform welding as well as grinding while wearing the multi-function face protector and that can be used with safety glasses, goggles and a mask. The multi-function face protector includes a head band, a forehead cover, and a face shield. The face shield comprises resilient hooks formed at its upper central portion, and engaging portions formed at its opposite ends respectively. The forehead cover comprises shield couplings formed at the central portion of its inner surface, and projections formed at the opposite ends of its inner surface respectively. The resilient hooks of the face shield are engaged with the respective shield couplings of the forehead cover.

2 Claims, 7 Drawing Sheets

[Fig 1]
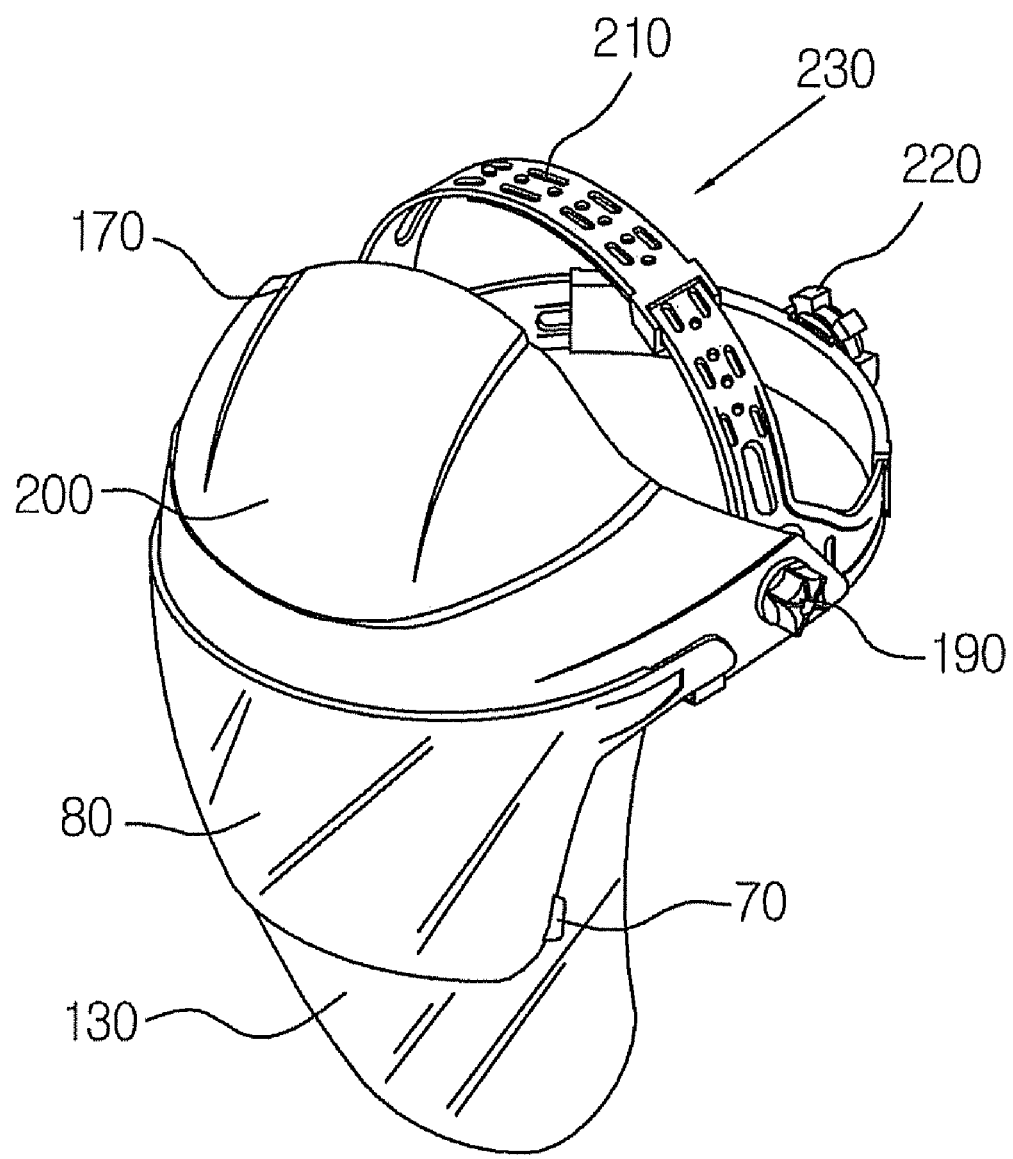

[Fig 2]
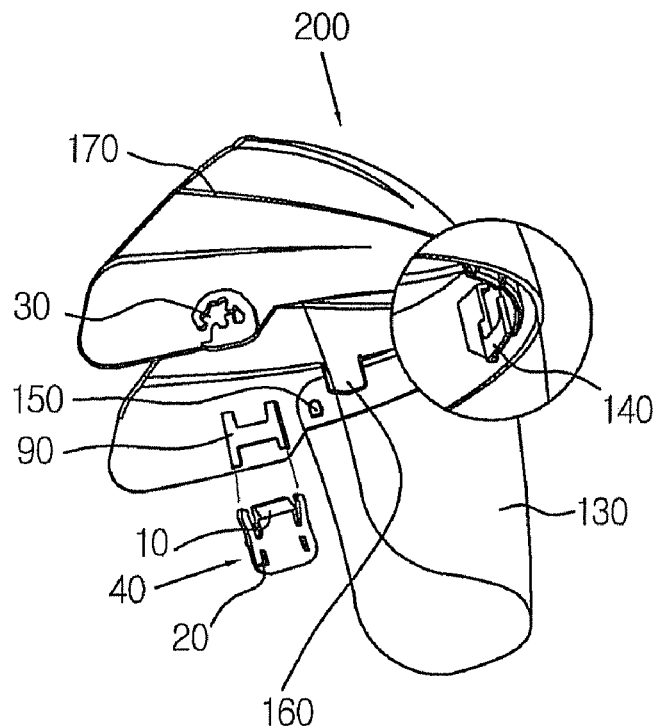
[Fig 3]
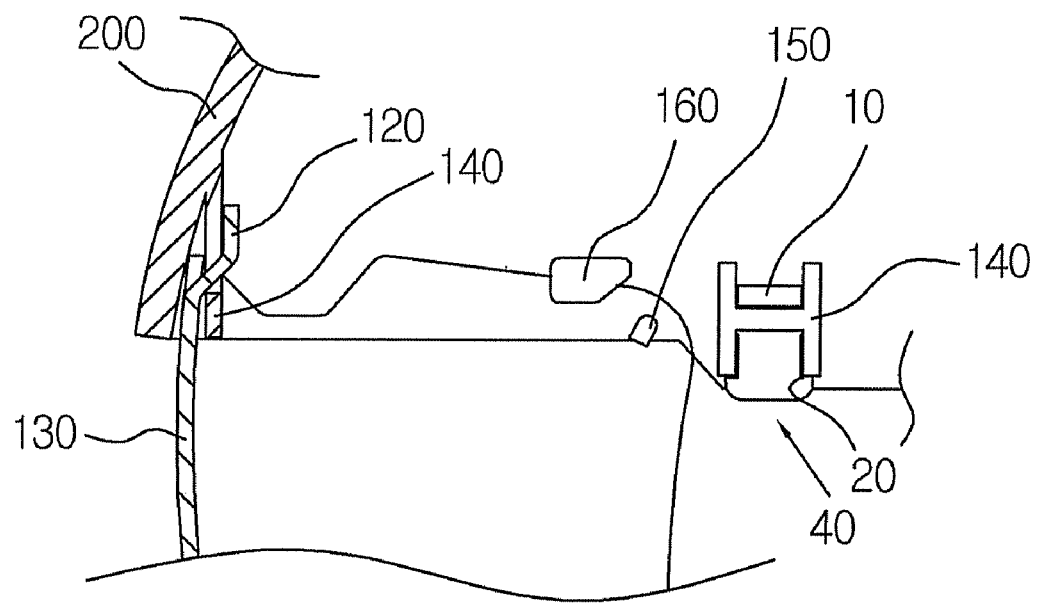

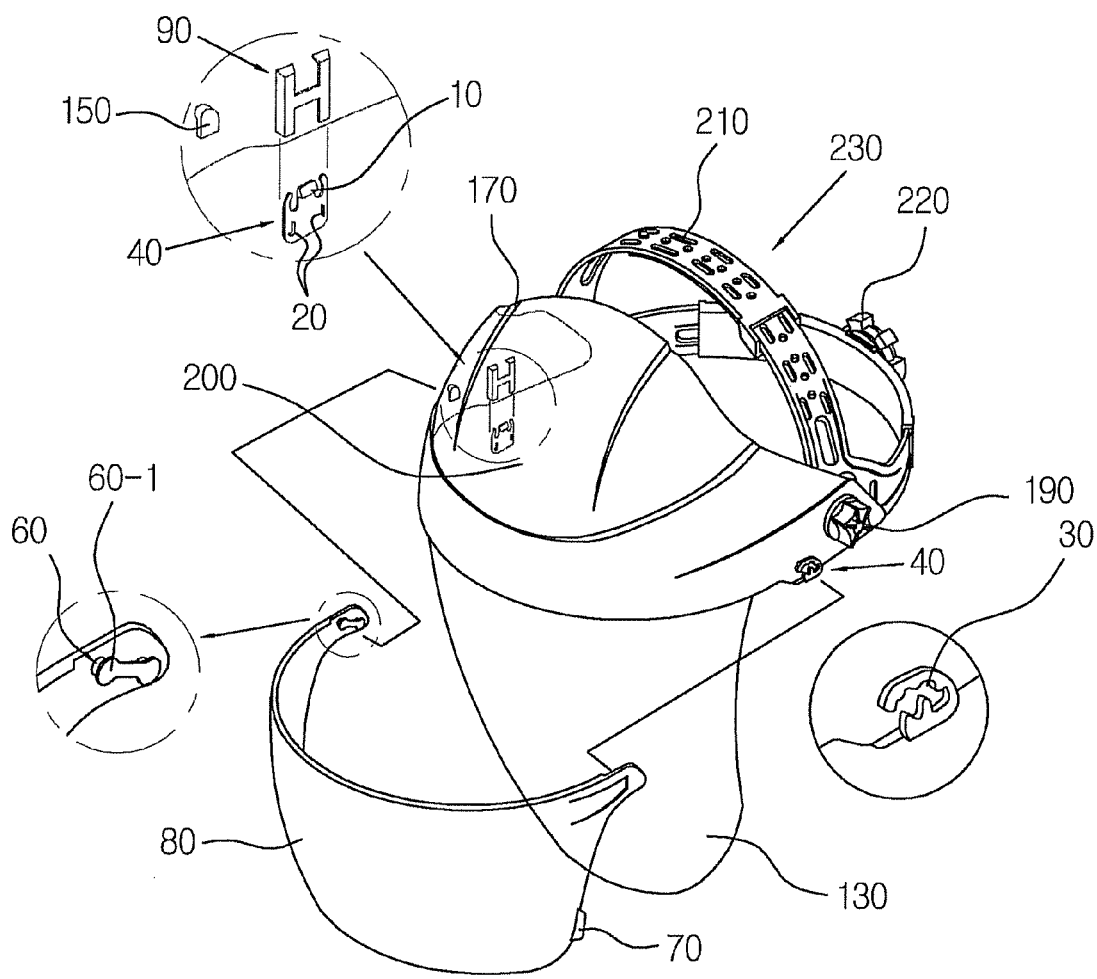
[Fig 4]

[Fig 5]
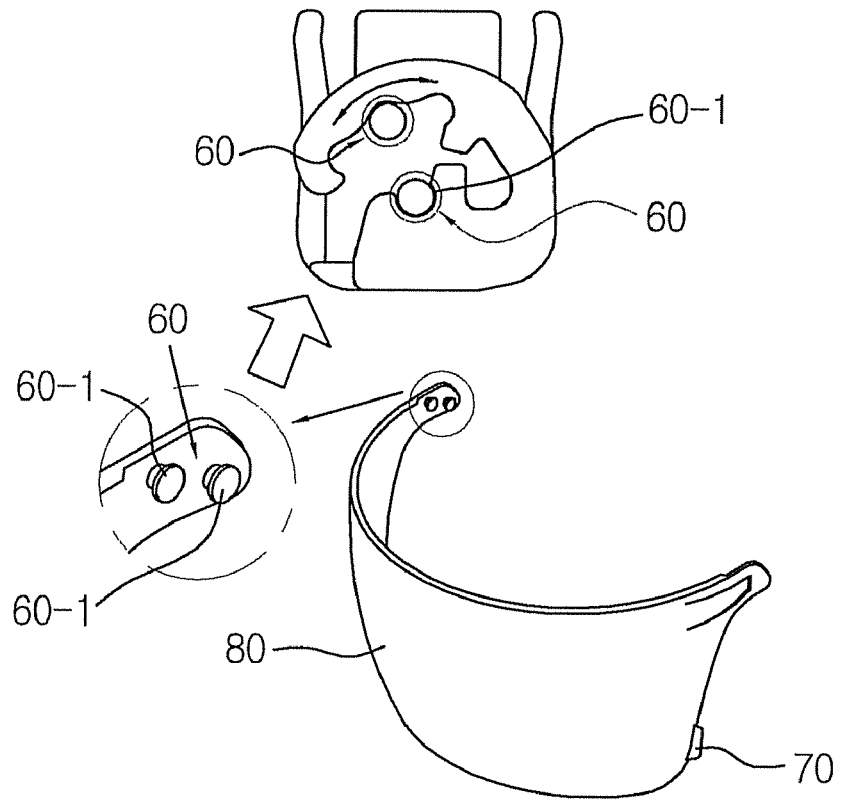
[Fig 6]
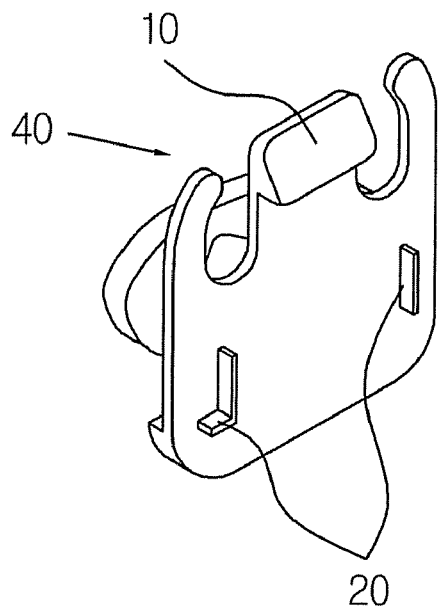

[Fig 7]
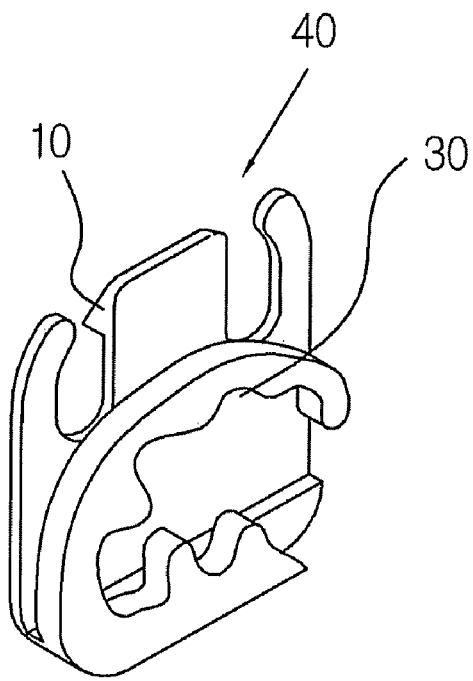
[Fig 8]
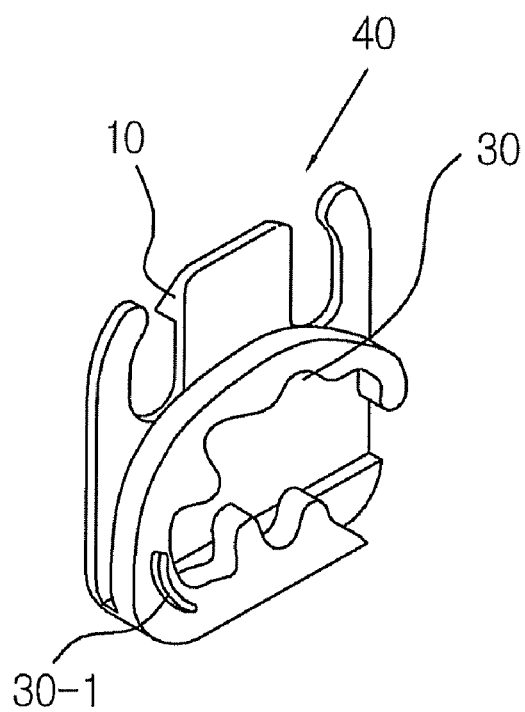

[Fig 9]
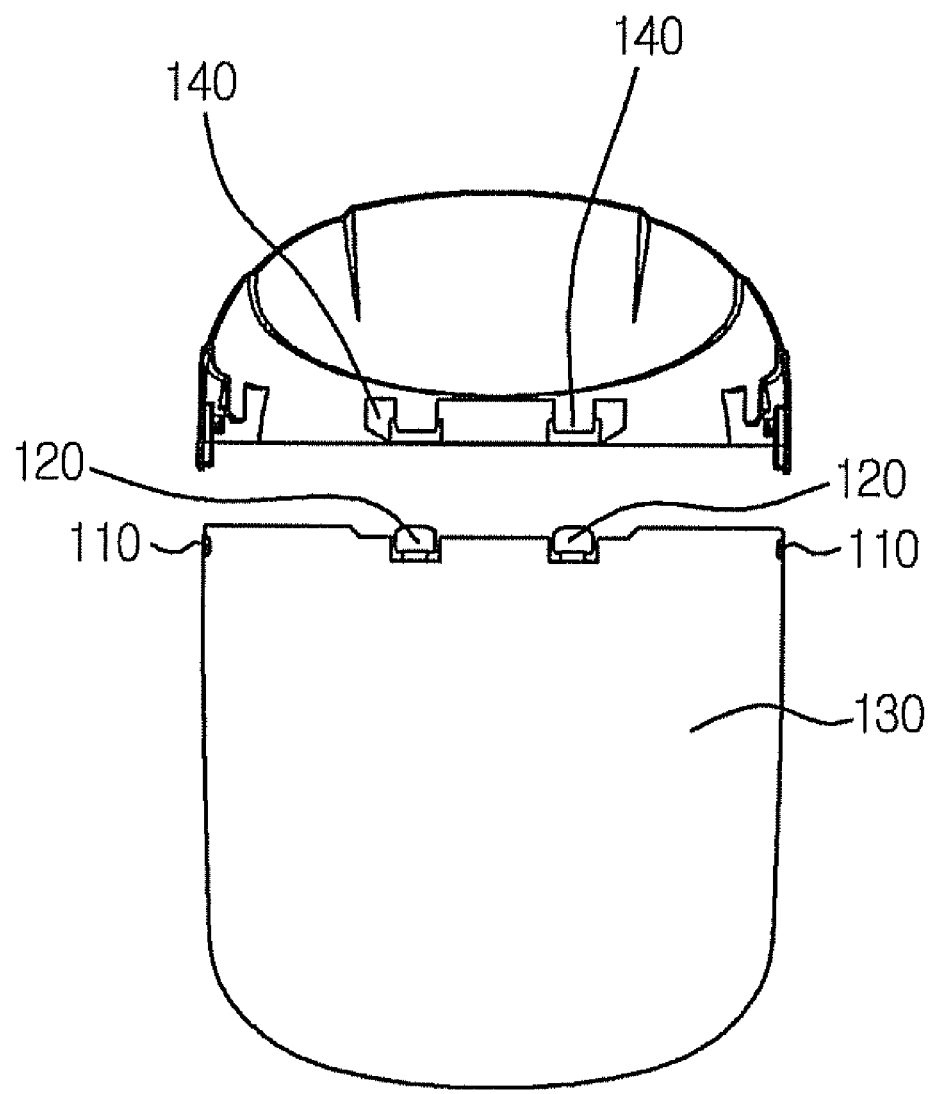

[Fig 10]
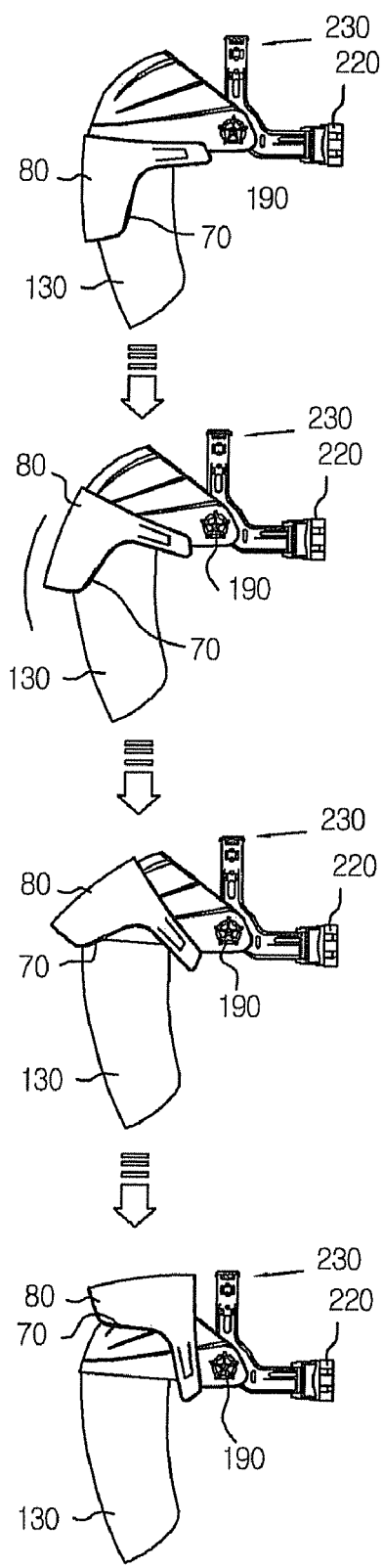

MULTI-FUNCTION FACE PROTECTOR

BACKGROUND OF THE INVENTION

1. Field of the Invention

The present invention relates to a multi-function face protector, more particularly, to a face protector having a protective shade that enables the worker to perform welding as well as grinding while wearing the multi-function face protector and that can be used with safety glasses, goggles and a mask.

2. Description of the Related Art

Generally, a face protector protects the face of the worker from materials scattered toward the worker during a certain process in the factory and the industrial field. The face protector can be used in processes such as cutting, drilling, mining and power woodworking in which scattered materials of high impact energy are generated. Further, the face protector can be used for cases such as grinding, machining, woodworking and lumbering in which scattered materials of relatively low impact energy may be generated. Yet further, the face protector can be used in processes such as furnacing iron, nonferrous metal or glass in which scattered materials of molten state may be generated. Yet further, the face protector can be used in processes in which scattered materials of liquid or floating dust may be generated.

The face protector is commonly divided into a type in which the face protector can be worn on the head of the worker and a type in which the face protector can be placed on a safety cap. The face protector placed on the safety cap is secured to the safety cap mainly by a frame and springs connecting the opposite ends of the frame. On a lower portion of the frame, a transparent or translucent protective plate is secured by rivets or the like.

The face protector includes springs, the rivet and other components which are made of metals having relatively heavy weight, so that the weight of the face protector is quite heavy. Thus, when using the face protector for a long time, there is a problem that the user becomes fatigued by the weight of the face protector. Further, when using the face protector for a long time, there is another problem that it is difficult to change only the protective plate in a case that the protective plate is scratched by the scattered materials.

The face protector has a wide field of view, but needs a separate shield for shading the light generated from welding.

SUMMARY OF THE INVENTION

The present invention has been made to solve the above problems, and it is an object of the present invention to provide a face protector having a protective shade that enables the worker to perform welding as well as grinding while wearing the multi-function face protector and that can be used with safety glasses, goggles and a mask.

Another object of the present invention is to provide the face protector having a protective shade of a novel structure capable of easily changing a shield plate and a protective shade plate, and capable of minimizing a weight felt by the worker when used by reducing the weight of it.

Yet another object of the present invention is to provide the face protector having a protective shade wherein a bottom of the shield plate is expanded so as to protect the neck as well as the whole face.

In accordance with one aspect of the present invention, the above and other objects can be accomplished by the provision of a multi-function face protector including a head band, a forehead cover, and a face shield, the face shield comprising: resilient hooks formed at the upper central portion of the face shield; and engaging portions formed at the opposite ends of the face shield respectively, and the forehead cover comprising: shield couplings formed at the central portion of the inner surface of the forehead cover; and projections formed at the opposite ends of the inner surface of the forehead cover respectively, wherein, the resilient hooks of the face shield are engaged with the respective shield couplings of the forehead cover.

The forehead cover further comprises guide grooves formed at the opposite sides of the forehead cover respectively so as to easily couple the face shield with the forehead cover.

The forehead cover has connector couplings formed at the opposite ends of its inner surface respectively, and the protective shade has connectors coupled with the opposite ends of its inner surfaces, wherein the connectors are engaged with the connector couplings respectively.

The face shield is configured so that its full surface may be three-dimensionally protruded like a human face, and increases in width toward its lower portion so that it may cover and protect the neck of the worker while working.

Each of the connectors has U-shape when viewed from the front side, each of the connectors is provided with an inserting projection and guide projections on its inner side, wherein each of the connectors is engaged with each of the connector couplings of the forehead cover by the inserting projection and the guide projections, each of the connectors is provided with plural indents on its outer side, and into the plural indents, hinging projections of the protective shade are inserted, wherein the protective shade stepwise hinges about the plural indents.

Each of the connectors is further provided with a reinforcing projection 30-1 on its outer side so as to enhance the resilience of the plural indents.

The hinging projections of the protective shade are provided with an 8-shaped separation-proof projection.

Each of the hinging projections is provided with an independent separation-proof projection.

BRIEF DESCRIPTION OF THE DRAWINGS

The foregoing and other objects and features of the present invention will be more clearly understood from the following detailed description taken in conjunction with the accompanying drawings, in which:

FIG. 1 is a perspective view illustrating a multi-function face protector in accordance with a preferred embodiment of the present invention;

FIG. 2 is a view illustrating a combined state of a forehead cover and a face shield of the multi-function face protector in accordance with a preferred embodiment of the present invention;

FIG. 3 is a sectional view of the multi-function face protector in accordance with a preferred embodiment of the present invention;

FIG. 4 is a view illustrating a separated state of a coupling and a connector coupling of the multi-function face protector in accordance with a preferred embodiment of the present invention;

FIG. 5 is a perspective view of the connector coupling of the multi-function face protector in accordance with a preferred embodiment of the present invention;

FIG. 6 is a side perspective view of the connector coupling of the multi-function face protector in accordance with a preferred embodiment of the present invention;

FIG. 7 is a side perspective view of the connector coupling of the multi-function face protector in accordance with a preferred embodiment of the present invention;

FIG. 8 is a side perspective view of the connector coupling of the multi-function face protector in accordance with another preferred embodiment of the present invention;

FIG. 9 is a view illustrating a combined state of the face shield of the multi-function face protector in accordance with a preferred embodiment of the present invention; and FIG. 10 is a view illustrating operating states of the protective shade of the multi-function face protector in accordance with a preferred embodiment of the present invention.

DESCRIPTION OF THE PREFERRED EMBODIMENTS

Preferred embodiments of the present invention will be described in detail with reference to the accompanying drawings, in which like components are denoted by the same reference numerals, and repetitious descriptions thereof will be omitted.

A multi-function face protector of the present invention is shown in FIGS. 1 to 10. The multi-function face protector includes a head band 230, a forehead cover 200, and a face shield 130. The forehead cover 200 and the face shield 130 are configured such that the face shield 130 is easily coupled with and separated from the forehead cover 200.

The face shield 130 includes resilient hooks 120 formed at its upper central portion, and engaging portions 110 formed at its opposite ends respectively, so as to couple with the forehead cover 200.

The forehead cover 200 includes shield couplings 140 and projections 150. The shield couplings 140 are formed at the central portion of the inner surface of the forehead cover 200. The projections 150 are formed at the opposite ends of the inner surface of the forehead cover 200 respectively.

The resilient hooks 120 of the face shield 130 are engaged with the respective shield couplings 140 of the forehead cover 200. The opposite engaging portions 110 of face shield 130 are engaged with projections 150 of the forehead cover 200 respectively.

The forehead cover 200 further includes guide grooves 160. The guide grooves 160 are formed at the opposite sides of the forehead cover 200 respectively so as to easily couple the face shield 130 with the forehead cover 200.

In such a configuration, when the face shield 130 is coupled with the forehead cover 200, the engaging portions 110 are engaged with the opposite projections 150 respectively, and then, the engaging portions 110 are pushed and inserted into the guide grooves 160 respectively.

Herein, the resilient hooks 120 are engaged with the shield couplings 140 of the forehead cover 200 respectively, so that each of the resilient hooks 120 is closely inserted into each of the shield couplings 140 by its resilience.

As such, the forehead cover 200 and the face shield 130 are closely coupled with each other. When separating the face shield 130 from the forehead cover 200, the forehead cover 200 and the face shield 130 are operated reversely to the coupling process. For instance, each of the resilient hooks 120 is depressed and drawn from each of the shield couplings 140, so that each of the resilient hooks 120 is separated from each of the shield couplings 140. Then, the engaging portions 110 are drawn from the respective opposite projections 150, so that the face shield 130 is completely separated from the forehead cover 200.

In such a way, the face shield 130 is coupled with and separated from the forehead cover 200.

Further, the head band 230 includes a size adjuster 210 at its upper end. The size adjuster 210 may adjust vertical circumferential size of the head band 230 according to the vertical circumferential size of the user's head. Thus, the size adjuster 210 may adjust the head band 230 so that eyes of the user are positioned at the central portion of the lens of the face shield.

The head band 230 also includes an adjusting lever 220. The adjusting lever 220 may adjust a horizontal circumferential size of the head band 230 according to the horizontal circumferential size of the user's head.

The forehead cover 200 is coupled with the head band 230 by screws 190 at its opposite sides.

The forehead cover 200 of the present invention has stepped portions 170 on its upper sides for aesthetic purpose.

The face shield 130 of the present invention is configured so that its full surface may be three-dimensionally protruded like a human face. Further, the face shield 130 of the present invention increases in width toward its lower portion so that it may cover and protect the neck of the worker while working.

Further, the forehead cover 200 may be coupled with a protective shade 80. The protective shade 80 and the forehead cover 200 are configured so that the protective shade 80 is stepwise raised against the forehead cover 200 as shown in FIG. 10. The forehead cover 200 has connector couplings 90 formed at the opposite ends of its inner surface respectively. The protective shade 80 has connectors 40 coupled with the opposite ends of its inner surface respectively. The connectors 40 are engaged with the connector couplings 90 respectively.

Each of the connectors 40 has U-shape when viewed from the front side as is apparent from FIGS. 6 and 7.

Each of the connectors 40 is provided with an inserting projection 10 and guide projections 20 on its inner side. Each of the connectors 40 is engaged with each of the connector couplings 90 of the forehead cover 200 by the inserting projection 10 and the guide projections 20.

Each of the connectors 40 is provided with plural indents 30 on its outer side. Into the plural indents 30, hinging projections 60 of the protective shade 80 are inserted. Thus, the protective shade 80 stepwise hinges about the plural indents 30. The hinging projections 60 of the protective shade 80 will be described in detail later.

According to another preferred embodiment of the present invention as shown in FIG. 8, each of the connectors 40 is further provided with a reinforcing projection 30-1 on its outer side so as to enhance the resilience of the plural indents 30.

The protective shade 80 has hinging projections 60 that are inserted into and coupled with the plural indents 30 of the connector 40 of the protective shade 80 shown in FIGS. 5 to 8. When the protective shade 80 is forced to hinge downwardly in the state that the hinging projections 60 are coupled with the plural indents 30, the hinging projections 60 are stopped at a first position of the plural indents 30. Herein, the protective shade 80 may be further forced to hinge downwardly, then the hinging projections 60 pass over the first position of the plural indents 30, and then stop at a second position of the plural indents 30. By this way, the protective shade 80 operates to hinge in conjunction with three stop positions as shown in FIG. 10.

As shown in FIG. 4, the hinging projections 60 of the protective shade 80 may be also provided with an 8-shaped separation-proof projection 60-1 connecting the hinging projections 60 so as to prevent the hinging projections 60 separating from the plural indents 30. The separation-proof projection 60-1 projects laterally from the sides of the hinging projections 60. Thus, when the hinging projections 60 are coupled with the plural indents 30, the separation-proof projection 60-1 may be engaged with the edge of the plural indents 30. Thus, the hinging projections 60 may not be separated from the plural indents 30.

As shown in FIG. 5, each of the hinging projections 60 may be provided with an independent separation-proof projection 60-1. Due to the independent separation-proof projection 60-1, contact between the connector 40 and the connecting portion of the hinging projections 60 may be obviated.

The multi-function face protector of the present invention may be used by optionally coupling with the protective shade if necessary. On use, the protective shade hinges in conjunction with three stop positions, so that the user may use the protective shade with an ability to stop it at necessary positions.

As is apparent from the above description, according to the present invention, the face shield has a three-dimensional configuration that is integrally molded and ergonomically designed so as to effectively protect the face and the neck of the user. Therefore, the user may use the multi-function face protector conveniently and the multi-function face protector suffers from little heat-deformation.

Further, according to the present invention, the multi-function face protector can be used with other protectors such as goggles and the mask in the workplaces in which the scattered materials of high impact energy, molten state, and heat may be generated.

Further, according to the present invention, the multi-function face protector includes the coupling structure for easily changing the face shield, and the protective shade hinging in conjunction with three stop positions, so that the user may use the protective shade with an ability to stop it at necessary positions. Therefore, the user may use the multi-function face protector conveniently and the multi-function face protector is very effective in a safety equipment industry.

It should be understood that the embodiments and the accompanying drawings as described above have been described for illustrative purposes and the present invention is limited by the following claims. Further, those skilled in the art will appreciate that various modifications, additions and substitutions are allowed without departing from the scope and spirit of the invention as set forth in the accompanying claims.

What is claimed is:

1. A multi-function face protector comprising,
   a face shield comprising:
      resilient hooks formed at the upper central portion of the face shield; and
      engaging portions formed at the opposite ends of the face shield respectively,
   a forehead cover comprising:
      shield couplings formed at the central portion of the inner surface of the forehead cover; and
      projections formed at the opposite ends of the inner surface of the forehead cover respectively; and
   a protective shade hinged to the forehead cover,
   wherein the resilient hooks of the face shield are engaged with the respective shield couplings of the forehead cover,
   wherein the forehead cover has connector couplings formed at the opposite ends of its inner surface respectively, and the protective shade has connectors coupled with the opposite ends of its inner surfaces, wherein the connectors are engaged with the connector couplings respectively, and
   wherein each of the connectors has U-shape when viewed from the front side,
   each of the connectors is provided with an inserting projection and guide projections on its inner side, wherein each of the connectors is engaged with each of the connector couplings of the forehead cover by the inserting projection and the guide projections, and
   each of the connectors is provided with plural indents on its outer side, and into the plural indents, hinging projections of the protective shade are inserted, wherein the protective shade stepwise hinges about the plural indents.

2. The multi-function face protector according to claim 1, wherein each of the hinging projections is provided with an independent separation-proof projection.

* * * * *